United States Patent [19]
Rahmin et al.

[11] Patent Number: 5,449,851
[45] Date of Patent: Sep. 12, 1995

[54] HIGHLY SELECTIVE N-OLEFIN ISOMERIZATION PROCESS USING ZSM-35

[75] Inventors: Iraj Rahmin, Turnersville, N.J.; Albin Huss, Jr., Chadds Ford; Daria N. Lissy, Glen Mills, both of Pa.; Donald J. Klocke, Somerdale; Werner O. Haag, Lawrenceville, both of N.J.

[73] Assignee: Mobil Oil Corporation, Fairfax, Va.

[21] Appl. No.: 49,586

[22] Filed: Apr. 19, 1993

Related U.S. Application Data

[63] Continuation of Ser. No. 760,287, Sep. 16, 1991, abandoned.

[51] Int. Cl.$^6$ .............................................. C07C 5/27
[52] U.S. Cl. .................................................. 585/671
[58] Field of Search .......................................... 585/671

[56] References Cited

U.S. PATENT DOCUMENTS

| | | | |
|---|---|---|---|
| 3,992,466 | 11/1976 | Plank et al. | 260/671 |
| 4,043,938 | 8/1977 | Reif et al. | 502/54 |
| 4,324,940 | 4/1982 | Dessau | 585/466 |
| 4,697,039 | 9/1987 | Schmidt | 585/478 |
| 4,749,819 | 6/1988 | Hamilton, Jr. | 585/329 |
| 4,788,364 | 11/1988 | Harandi | 585/312 |
| 4,886,925 | 12/1989 | Harandi | 585/331 |
| 4,922,048 | 5/1990 | Harandi | 585/310 |
| 4,967,032 | 10/1990 | Ho et al. | 585/530 |
| 4,996,386 | 2/1991 | Hamilton, Jr. et al. | 585/646 |

FOREIGN PATENT DOCUMENTS

| | | |
|---|---|---|
| 0026041 | 4/1981 | European Pat. Off. . |
| 0247802 | 12/1987 | European Pat. Off. . |
| 0501577 | 2/1992 | European Pat. Off. . |
| 0523838 | 6/1992 | European Pat. Off. . |

*Primary Examiner*—Asok Pal
*Attorney, Agent, or Firm*—Alexander J. McKillop; Dennis P. Santini; Laurence P. Hobbes

[57] ABSTRACT

A process is disclosed for the highly selective skeletal isomerization of linear olefin-containing organic feeds wherein linear olefins, e.g., n-butenes, are contacted with catalyst comprising ZSM-35 under isomerization conditions to produce iso-olefins of corresponding carbon number, e.g., isobutene. High iso-olefin selectivities thus can be obtained, even at relatively low temperatures and high linear olefin partial pressures.

26 Claims, 4 Drawing Sheets

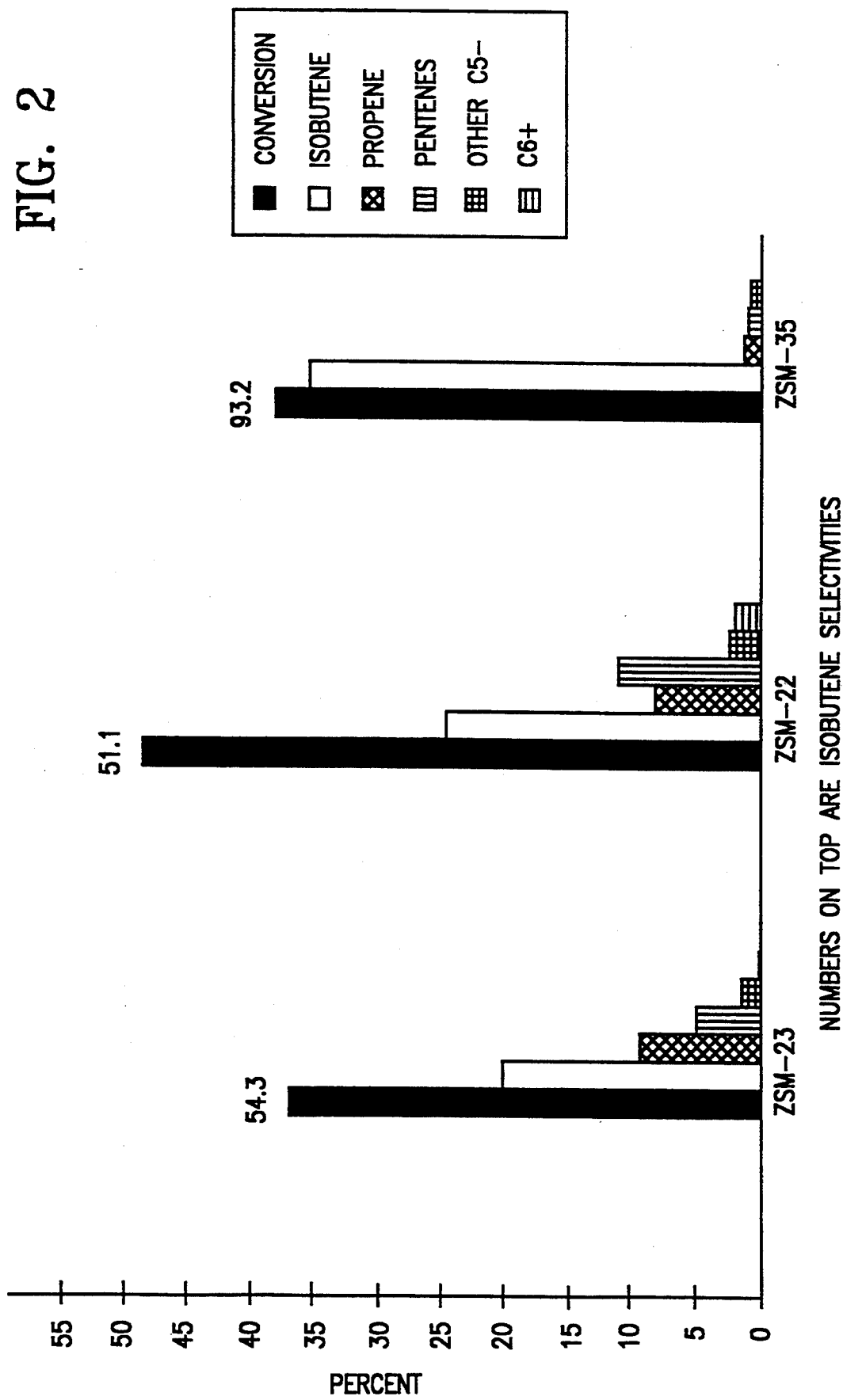

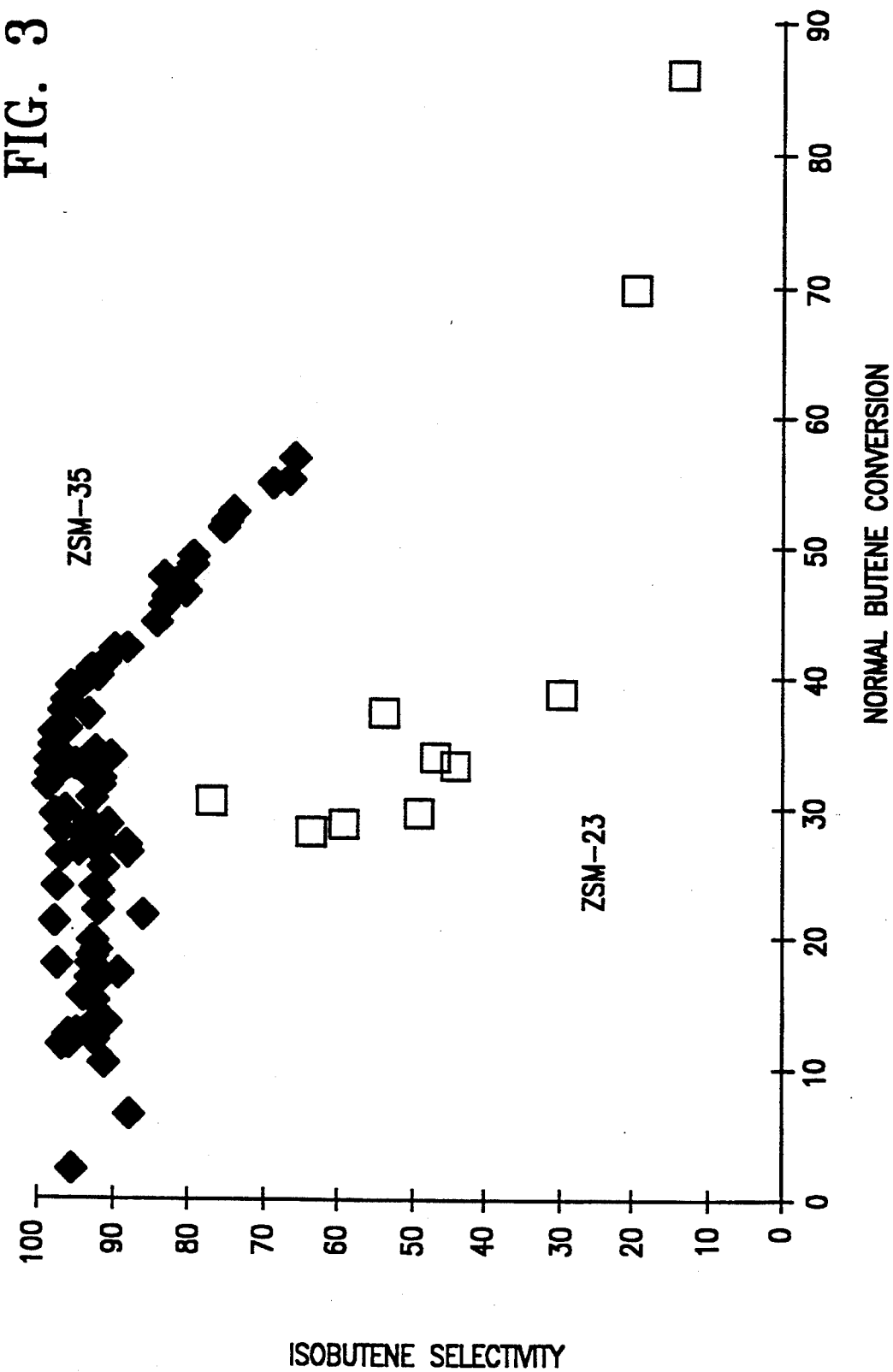

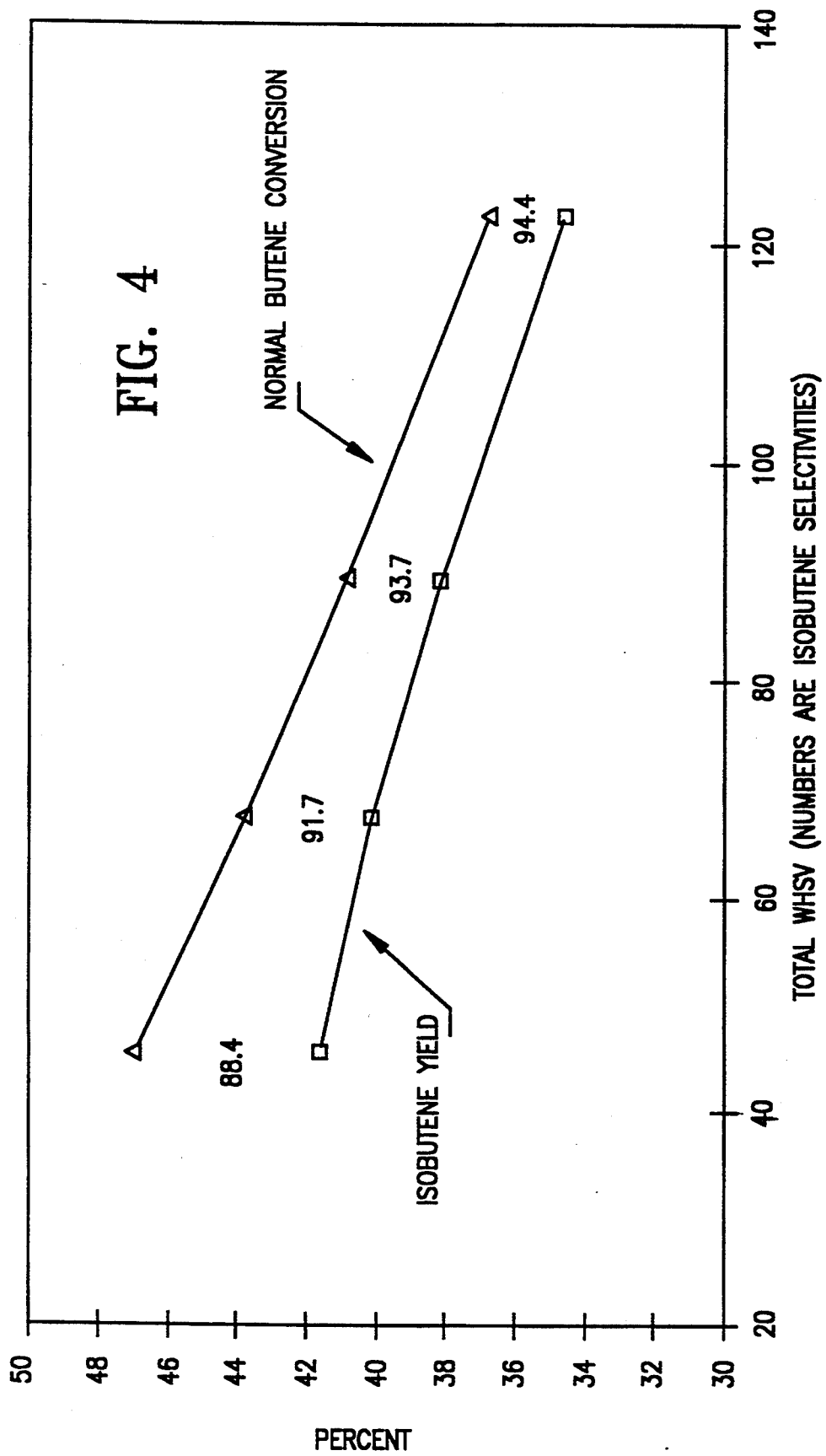

HIGHLY SELECTIVE N-OLEFIN ISOMERIZATION PROCESS USING ZSM-35

This is a continuation of application Ser. No. 07/760,287 filed on Sep. 16, 1991, now abandoned.

FIELD OF THE INVENTION

This invention relates to a highly selective method for the conversion of n-olefin-containing, e.g. n-butene-containing, hydrocarbon streams to iso-olefin-rich, e.g., isobutene-rich product streams. The process uses a catalyst composition comprising ZSM-35 or its isotypes and can achieve isobutene selectivities of greater than 90% or even 99% at substantial n-butene conversions.

BACKGROUND OF THE INVENTION

The demand for iso-alkenes has recently increased. For example, relatively large amounts of isobutene are required for reaction with methanol or ethanol over an acidic catalyst to produce methyl tert-butyl ether (MTBE) or ethyl tert-butyl ether (ETBE) which is useful as an octane enhancer for unleaded gasolines. Isoamylenes are required for reaction with methanol over an acidic catalyst to produce tert-amyl methyl ether (TAME). With passage of the Clean Air Act in the United States mandating increased gasoline oxygenate content, MTBE, ETBE and TAME have taken on new value as a clean-air additive, even for lower octane gasolines. Lead phasedown of gasolines in Western Europe has further increased the demand for such oxygenates.

An article by J. D. Chase, et al., *Oil and Gas Journal*, Apr. 9, 1979, discusses the advantages one can achieve by using such materials to enhance gasoline octane. The blending octane values of MTBE when added to a typical unleaded gasoline base fuel are RON=118, MON=101, R+M /2=109. The blending octane values of TAME when added to a typical unleaded gasoline base fuel are RON=112, MON=99, R+M /2=106. Isobutene (or isobutylene) is in particularly high demand as it is reacted with methanol to produce MTBE.

The addition of shape-selective zeolite additives such as ZSM-5 to cracking catalysts, e.g. those used in fluidized catalytic cracking (FCC), is beneficial in producing gasoline boiling range product of increased octane rating. However, increased amounts of olefins result, including n-butenes, creating a need for their conversion to higher value products such as isobutene which can be used to produce MTBE.

Butene exists in four isomers: butene-1, cis-butene-2, its stereo-isomer trans-butene-2, and isobutene. Conversions between the butenes-2 is known as geometric isomerization, whereas that between butene-1 and the butenes-2 is known as position isomerization, double-bond migration, or hydrogen-shift isomerization. The aforementioned three isomers are not branched and are known collectively as normal or n-butenes. Conversion of the n-butenes to isobutene, which is a branched isomer, is widely known as skeletal isomerization.

The reaction of tertiary olefins with alkanol to produce alkyl tertiary alkyl ether is selective with respect to iso-olefins. Linear olefins are unreactive in the acid catalyzed reaction, even to the extent that it is known that the process can be utilized as a method to separate linear and iso-olefins. The typical feedstream of FCC $C_4$ or $C_{4+}$ crackate used to produce tertiary alkyl ethers in the prior art which contains normal butene and isobutene utilizes only the branched olefin in etherification. This situation presents an exigent challenge to workers in the field to discover a technically and economically practical means to utilize linear olefins, particularly normal butene, in the manufacture of tertiary alkyl ethers.

In recent years, a major development within the petroleum industry has been the discovery of the special catalytic capabilities of a family of zeolite catalysts based upon medium pore size shape selective metallosilicates. Discoveries have been made leading to a series of analogous processes drawn from the catalytic capability of zeolites in the restructuring of olefins.

European Patent 0026041 to Garwood, incorporated herein by reference, discloses a process for the restructuring of olefins in contact with zeolite catalyst to produce iso-olefins, followed by the conversion of iso-olefins to MTBE and TAME. The restructuring conditions comprise temperature between 204° C. and 315° C. and pressure below 51 kPa.

In European Patent 0247802 to Barri et al., it is taught that linear olefins can be restructured in contact with zeolite catalyst, including Theta-1 (ZSM-22) and ZSM-23, to produce branched olefins. The restructuring conditions comprise temperature between 200°–550° C., pressure between 100 and 5000 kPa and WHSV between 1 and 100. Selectivities to isobutene up to 91.2% are reported using a calcined Theta-1 tectometallosilicate at 400° C. and 30.6% 1-butene conversion.

U.S. Pat. No. 3,992,466 to Plank et al. teaches the use of ZSM-35 as a catalyst for hydrocarbon conversion reactions, including "isomerization of aromatics, paraffins and olefins."

U.S. Pat. No. 4,922,048 to Harandi discloses the use of a wide variety of medium pore size zeolites, e.g. $ZSM-5$, $ZSM-11$, $ZSM-12$, $ZSM-22$, $ZSM-23$, ZSM-35 and $ZSM-48$, in low temperature (232°–385° C.) olefin interconversion of $C_2$–$C_6$ olefins to products including tertiary $C_4$–$C_5$ olefins and olefinic gasoline.

U.S. Pat. No. 4,886,925 to Harandi discloses low pressure high temperature conversion of light olefins to produce higher olefins rich in isoalkenes. The process converts $C_{2+}$ n-alkenes to a product comprising $C_4$–$C_6$ alkenes rich in iso-alkenes, $C_{7+}$ olefinic gasoline boiling range hydrocarbons, and unconverted hydrocarbons over ZSM-5. The reference teaches further treatment of the alkene effluent with methanol in the presence of medium pore size zeolites such as ZSM-5, ZSM-11, ZSM-12, ZSM-35, ZSM-38 and ZSM-48.

U.S. Pat. No. 4,996,386 to Hamilton, Jr. discloses concurrent isomerization and disproportionation of hydrocarbon olefins using a ferrierite/Mo/W/$Al_2O_3$ catalyst. The catalyst exemplified produces fewer branched olefins than a comparable material free of ferrierite and the reference teaches that ferrierite-containing catalysts exhibit improved selectivity to linear olefins than conventionally prepared disproportionation catalysts.

All of the above references are incorporated herein by reference.

Despite the efforts exemplified in the above references, the skeletal isomerization of olefins e.g., to produce isobutene, has been hampered by relatively low selectivity to isobutene perhaps owing to the lability of these olefins. It is further known that skeletal isomerization becomes more difficult as hydrocarbons of lower molecular weight are used, requiring more severe operating conditions, e.g. higher temperatures and lower linear olefin partial pressures.

Generally, the conversion of n-butenes to iso-butene is conducted at selectivities below 90%. In order to obtain higher selectivities, operation at high temperatures (>500° C.) and with high nitrogen feed dilution (butene partial pressure, typically less than 5 psia (34.5 kPa)) is generally required. Selectivities of greater than 90%, 95% or even 99% are highly advantageous in commercial conversion of n-butenes to isobutene in order to avoid the need to separate out materials other than n-butene from the product stream. Such high selectivities will permit direct introduction (cascading) or indirect introduction of the isomerizer effluent to an etherification zone where isobutene is reacted with alkanol to produce alkyl tert-butyl ether, e.g. MTBE. Unconverted n-butenes in the isomerizer effluent can be withdrawn either before the etherification zone or preferably, from the etherification zone effluent insofar as the etherification reaction utilizes only the isobutene component of the isomerizer stream. Unreacted n-butenes from the etherification zone effluent can be recycled to the isomerizer where they are converted to isobutene at high selectivity. If the recycle stream contains not only unconverted linear olefins, e.g. n-butenes, but also by-product such as other olefins (e.g. propylene) or paraffins, they have to be removed from the recycle stream, such as by distillation or by taking a slip stream. These removal steps are expensive and can lead to considerable loss of not only the by-products but butenes as well. These losses are larger when the by-products formed are present in higher concentration. Thus, even small improvements in the isobutene selectivity during n-butene isomerization have a major effect on the commercial viability of the process. However, high selectivities in skeletal isomerization processes have generally required low linear olefin partial pressures and high temperatures which place substantial limitations on such processes. It would, therefore, be advantageous to provide a skeletal isomerization catalyst capable of maintaining relatively high selectivity at low temperatures and high linear olefin partial pressures.

SUMMARY OF THE INVENTION

The present invention provides a method for highly selective conversion of linear olefins to corresponding iso-olefins of the same carbon number, e.g. n-butenes to isobutene, which comprises contacting a linear olefin-containing organic feedstock with a catalyst comprising ZSM-35 under skeletal isomerization conditions.

The high selectivity of ZSM-35 in the present invention results in large part from isomerization occurring without significant conversion to lighter and heavier molecules. This phenomenon, it is believed, is a consequence of the pore structure of ZSM-35 which promotes isomerization at a much faster rate than the reaction by which say, butene, is converted to lighter (mostly propylene) and heavier olefins (olefin interconversion reaction). Moreover, such isomerization takes place without significant cracking of the feed or hydrogenation or dehydrogenation effects resulting in the formation of, say, n-butane or butadiene. The present invention can be used to effect conversion of linear olefins to iso-olefins while resulting in less than 30%, 10%, 5% or even less than 1% by weight of converted product having lower or higher average carbon number.

DESCRIPTION OF THE FIGURES

FIG. 2 depicts the respective conversions and products obtained for ZSM-22, ZSM-23 and ZSM-35 in skeletal isomerization of 1-butene at 400° C.

FIG. 3 is a selectivity/conversion plot comparing the performance of ZSM-23 and ZSM-35.

FIG. 4 depicts the conversions and products obtained for ZSM-35 in skeletal isomerization of 1-butene at high WHSV, low temperatures and high butene partial pressures.

DETAILED DESCRIPTION OF THE INVENTION

Figure 1:
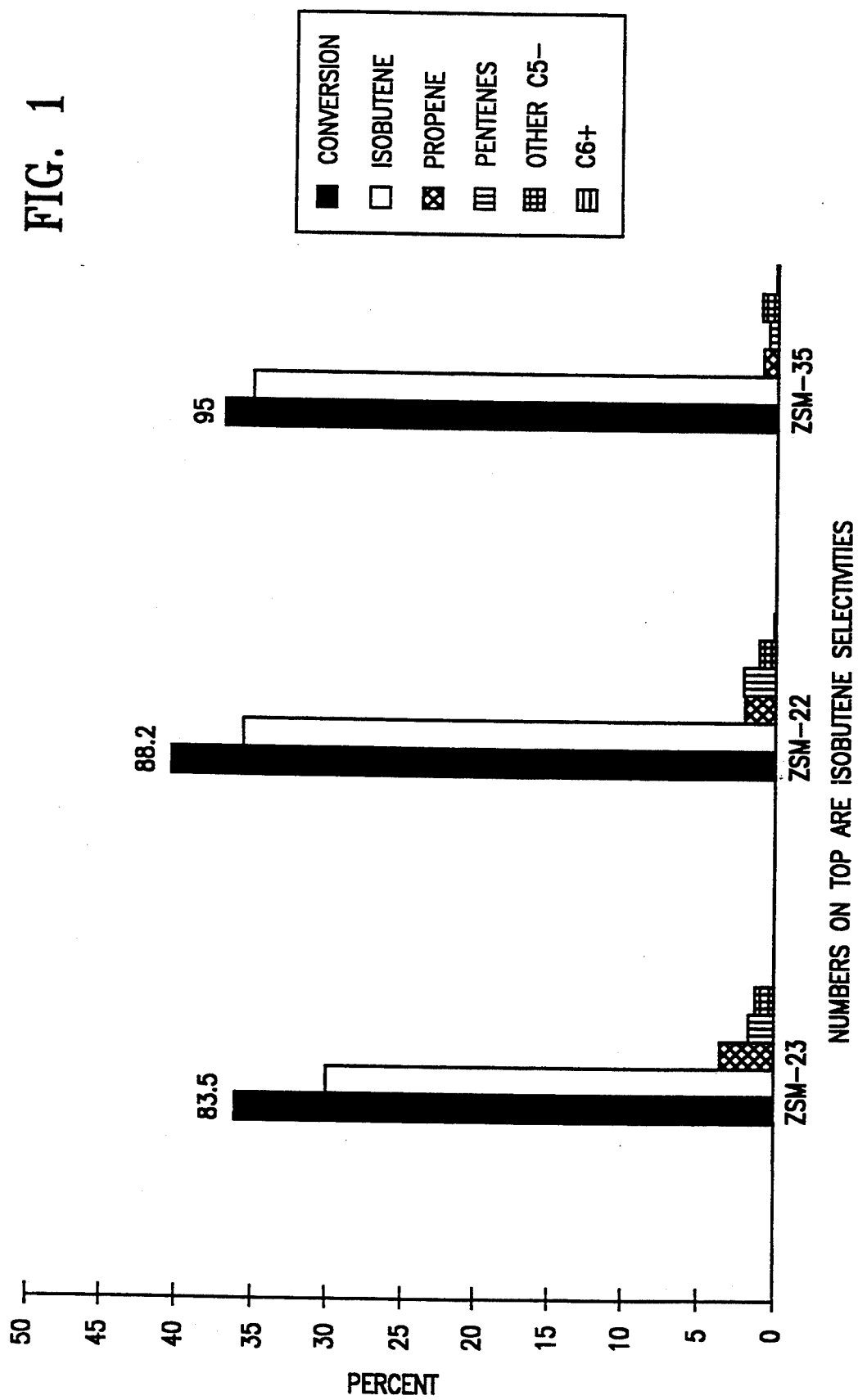
FIG. 1 depicts the respective conversions and products obtained for ZSM-22, ZSM-23 and ZSM-35 in skeletal isomerization of 1-butene at 550° C.

The present invention provides a process which converts a linear olefin-containing hydrocarbon feedstream to an iso-olefin rich product at high iso-olefin selectivity over a catalyst comprising ZSM-35 under skeletal isomerization conditions.

For present purposes, "ZSM-35" is considered equivalent to its isotypes, which include ferrierite (P. A. Vaughan, Acta Cryst. 21, 983 (1966)); FU-9 (D. Seddon and T. V. Whittam, European Patent B-55,529, 1985); ISI-6 (N. Morimoto, K. Takatsu and M. Sugimoto, U.S. Pat. No. 4,578,259, 1986); monoclinic ferrierite (R. Gramlich-Meier, V. Gramlich and W. M. Meier, Am. Mineral. 70, 619 (1985)); NU-23 (T. V. Whittam, European Patent A-103,981, 1984); and Sr-D (R. M. Barrer and D. J. Marshall, J. Chem. Soc. 1964, 2296 (1964)). Preferably the catalyst comprises ZSM-35 in its hydrogen-exchanged form, HZSM-35.

The skeletal isomerization reaction of the present invention is carried out at temperatures between 250 and 750° C.; weight hourly space velocity based on linear olefin in the feed between 5 and 500 WHSV; and linear olefin partial pressure between 12 and 500 kPa. The preferred conditions are temperatures between 325 and 600° C., more preferably between 390 and 550° C., WHSV between 10 and 400, more preferably between 30 and 250; and a linear olefin partial pressure between 30 and 300 kPa, more preferably between 50 and 150 kPa. Under these conditions the conversion of linear olefin, e.g., n-butene, can be at least 10%, preferably at least 25% and more preferably at least 35%. The selectivity to iso-olefin, e.g., isobutene, is at least 75%, preferably at least 85%, 90%, 95% or even 99%.

The present invention is especially suited to processes carried out at high linear olefin to iso-olefin selectivity, e.g., at least 92% at relatively low conversion temperatures and high linear olefin partial pressures. Such processes can maintain selectivities of at least 90, 92 or 95% at a conversion temperature less than or equal to 550, 400 or even 350° C., and linear olefin partial pressures above 2 psia (14 kPa), e.g. above 5 psia (34 kPa). Such processes can be carried out at an overall conversion of linear olefins of at least 30 wt %.

Preferred feedstreams include $C_4$ or $C_{4+}$ hydrocarbon feedstreams. Linear olefins suited to use in the present invention may be derived from a fresh feedstream, preferably comprising n-butenes and/or n-pentenes, or from the effluent of an iso-olefin etherification reactor which employs alkanol and $C_4$ or $C_{4+}$ hydrocarbon feedstock. Typical hydrocarbon feedstock materials for isomerization reactions according to the present invention include olefinic streams, such as cracking process light gas containing butene isomers in mixture with substantial amounts of paraffins including n-butane and isobutane. The C4 components usually contain a major amount of unsaturated compounds, such as 10–40% isobutene, 20–55% linear butenes, and small amounts of butadiene. Also, C4+ heavier olefinic hydrocarbon streams may be used, e.g. C4 to C10, preferably C4 to C6 olefinic hydrocarbon streams.

ZSM-35 is more particularly described in U.S. Pat. No. 4,016,245, the entire contents of which are incorporated herein by reference.

An example of a piperidine-derived ferrierite is more particularly described in U.S. Pat. No. 4,343,692, the entire contents of which are incorporated herein by reference. Other synthetic ferrierite preparations are described in U.S. Pat. Nos. 3,933,974; 3,966,883; 4,000,248; 4,017,590; and 4,251,499, the entire contents of all being incorporated herein by reference. Further descriptions of ferrierite are found in Bibby et al, "Composition and Catalytic Properties of Synthetic Ferrierite," Journal of Catalysis, 35, pages 256–272 (1974).

The zeolite catalyst used is preferably at least partly in the hydrogen form, e.g. HZSM-35, but other cations, e.g. rare earth cations, may also be present. When the zeolites are prepared in the presence of organic cations, they may be quite inactive possibly because the intracrystalline free space is occupied by the organic cations from the forming solution. The zeolite may be activated by heating in an inert atmosphere to remove the organic cations e.g. by heating at over 500° C. for 1 hour or more. The hydrogen form can then be obtained by base exchange with ammonium salts followed by calcination e.g. at 500° C. in air. Other cations, e.g. metal cations, can be introduced by conventional base exchange or impregnation techniques.

The ZSM-35 may be incorporated in another material usually referred to as a matrix or binder. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

Of all the foregoing materials, silica may be preferred as the matrix material owing to its relative inertness for catalytic cracking reactions which are preferably minimized in the instant isomerization processes. The relative proportions of finely divided ZSM-35 and inorganic oxide gel matrix vary widely with the zeolite content ranging from about 1 to about 90 percent by weight and more usually in the range of about 30 to about 80 percent by weight of the composite.

The regeneration of spent zeolite catalyst used in the isomerization reaction is carried out oxidatively or hydrogenatively employing procedures known in the art. The catalyst of the present invention can be readily reactivated without significantly reducing selectivity for isobutene by exposing it to hydrogen for a suitable period, e.g. overnight.

In order to obtain desired linear olefin skeletal isomerization activity/selectivity, ZSM-35, preferably in the hydrogen form, should have an alpha value of at least 5, preferably at least 50 when used in the catalyst of the present invention. Alpha value, or alpha number, of a zeolite is a measure of zeolite acidic functionality and is more fully described together with details of its measurement in U.S. Pat. No. 4,016,218, *J. Catalysis*, 6, pp. 278–287 (1966) and *J. Catalysis*, 61, pp. 390–396 (1980). The experimental conditions cited in the latter reference are used for characterizing the catalysts described herein.

Example 1

Preparation of As-Synthesized ZSM-35

1.18 parts of aluminum sulfate (17.2% $Al_2O_3$) were added to a solution containing 9.42 parts $H_2O$ and 1.38 parts of 50% NaOH solution in an autoclave. 0.03 parts of ZSM-35 seeds and 3.20 parts of Hi-Sil precipitated silica were added with agitation, followed by 1.0 part of pyrrolidine.

The reaction mixture had the following composition, in mole ratios:

| | |
|---|---|
| $SiO_2/Al_2O_3$ | 21.5 |
| $OH^-/SiO_2$ | 0.11 |
| $H_2O/Al_2O_3$ | 13.5 |
| $R/Al_2O_3$ | 6.45 | where R=pyrrolidine. The mixture was crystallized at 105° C. for 74 hours with stirring. The ZSM-35 product was filtered, washed with deionized water, and dried at 120° C. The chemical composition of the product was, in weight percent:

| | |
|---|---|
| $SiO_2$ | 76.7 |
| $Al_2O_3$ | 6.4 |
| Na | 0.84 |
| C | 7.26 |
| N | 2.03 |
| Ash @ 1000° C. | 85.5 | with a silica/alumina ratio for the product, in moles, of 20.3/1.

Example 2

Preparation of HZSM-35/$SiO_2$ Mi

The as-synthesized ZSM-35 of Example 1 was calcined in nitrogen for 3 hours at 538° C., then exchanged two times at room temperature with 1 N $NH_4NO_3$ solution to convert it to the ammonium form, dried at 120° C., and calcined in air for 6 hours at 538° C. to convert it to the hydrogen form. The zeolite was dry mixed with a precipitated silica, in proportion to give 65% ZSM-35 / 35% silica after calcination, formed into pellets, and calcined in air for 3 hours at 538° C.

Example 3
Preparation of Silica-Bound HZSM-35

A catalyst was prepared by dry mixing the as-synthesized ZSM-35 of Example 1 with precipitated silica, in proportion to give, after calcination, 65% ZSM-35/35% silica in the catalyst. A solution containing 2% NaOH (based on solids) was added to the mix to create an extrudable mull, the mix was extruded to 1/16 inch (1.6 mm) diameter and dried at 120° C. The extrudate was exchanged two times with 1N $NH_4NO_3$ solution at room temperature, rinsed with deionized water, dried at 120° C. and calcined in nitrogen for 3 hours at 538° C. It was again exchanged with 1N $NH_4NO_3$ solution two times at room temperature, dried at 120° C., and calcined in air for 9 hours at 538° C.

Example 4
Preparation of Silica-Bound HZSM-35

A catalyst was prepared by dry mixing the as-synthesized ZSM-35 of Example 1 with precipitated silica. Colloidal silica, in proportion to give 65% ZSM-35/35% silica after calcination, and water were added to the dry mix to obtain an extrudable mull. The mull was extruded to 1/16 inch (1.6 mm) diameter, dried at 120° C., calcined in nitrogen for three hours at 538° C., and then in air for 6 hours at 538° C. The extrudate was exchanged two times with 1N $NH_4NO_3$ solution at room temperature, dried at 120° C. and calcined in nitrogen for 3 hours at 538° C.

Example 5
Isomerization of 1-Butene with ZSM-22, ZSM-23 and ZSM-35 at 550° C.

ZSM-22 was prepared by charging 48.2 parts water to an autoclave followed by 5.0 parts KOH solution (45% by weight), 1.0 part aluminum sulfate (17.2% $Al_2O_3$) and 0.45 parts seeds. After mixing thoroughly, 8.2 parts of Ultrasil VN3 precipitated silica (Nasilco), then 3.6 parts of ethylpyridinium bromide (50% by weight) were added and mixed thoroughly. After aging the reaction mixture for 16 hours at 93° C. while stirring, the temperature was increased to 160° C. and maintained until crystallization was complete. The product was identified as ZSM-22 by X-ray diffraction. The slurry was filtered, washed and dried. A portion of the zeolite was calcined in flowing nitrogen for 3 hours at 538° C. and 3 hours in air at the same temperature. The cooled zeolite was exchanged with 1 N $NH_4NO_3$ (5 cc/g zeolite) at room temperature for one hour then washed with water. The exchange procedure was repeated and the catalyst dried at 120° C. The zeolite was then calcined in flowing air for 3 hours at 538° C., then blended 65 parts zeolite and 35 parts Ultrasil VN3 and pelleted. The pellets were sized 14/24 mesh and recalcined at 538° C. in flowing air for 3 hours.

ZSM-23 was prepared by charging 85.5 parts water to an autoclave followed by 2.64 parts KOH solution (45% by weight), 1.0 part aluminum sulfate (17.2% $Al_2O_3$) and 0.5 parts ZSM-23 seeds (100% basis). After mixing thoroughly, 14.5 parts of Ultrasil VN3 precipitated silica (Nasilco), then 5.1 parts of pyrrolidine were added and mixed thoroughly. The autoclave was heated to 160° C. with stirring and maintained at these conditions until crystallization was complete. The product was identified as ZSM-23 by X-ray diffraction. After flashing the pyrrolidine, the slurry was cooled, washed, filtered and dried. Eight parts of the dried ZSM-23 were combined with 1 part Ultrasil VN3 and 1 part Ludox colloidal silica (DuPont), mulled and extruded to form 1/16 inch pellets which were dried at 120° C. The pellets were then calcined in flowing nitrogen for 2 hours at 538° C. and 3 hours in air at the same temperature. The cooled catalyst was exchanged with 1N $NH_4NO_3$ (5 cc/g catalyst) at room temperature for one hour then washed with water. The exchange procedure was repeated and the catalyst dried at 120° C. The exchanged extrudate was then calcined at 538° C. in flowing air for 3 hours.

The above-prepared ZSM-22 and ZSM-23, and ZSM-35 prepared in accordance with Example 3 above were used in butene skeletal isomerization reactions. The approximate experimental conditions were:

| | |
|---|---|
| Temperature | 550° C. |
| Pressure | 177 kPa |
| 1-Butene WHSV | 65 hr$^{-1}$ |
| $N_2$/Butene in feed | 3 vol/vol |

FIG. 1 graphically depicts the respective conversions and products obtained for ZSM-22, ZSM-23 and ZSM-35. Under these conditions selectivities of 83 5%, 88 2% and 95% respectively, were obtained.

Example 6
Isomerization of 1-Butene with ZSM-22, ZSM-23 and ZSM-35 at 400° C.

ZSM-22 and ZSM-23 prepared in accordance with Example 5, and ZSM-35 prepared in accordance with Example 3 above were used in butene skeletal isomerization reactions. The approximate experimental conditions were:

| | |
|---|---|
| Temperature | 400° C. |
| Pressure | 177 kPa |
| 1-Butene WHSV | 65 hr$^{-1}$ |
| $N_2$/Butene in feed | 3 vol/vol |

FIG. 2 graphically depicts the respective conversions and products obtained for ZSM-22, ZSM-23 and ZSM-35. Under these conditions selectivities of 54.3%, 51.1% and 93.2%, respectively, were obtained. ZSM-35 maintains selectivity above 90% even at temperatures which significantly reduce selectivities for ZSM-22 and ZSM-23.

Example 7
Isomerization of Butene with ZSM-23 and ZSM-35 at 400° C.

ZSM-22 and ZSM-23 prepared in accordance with Example 5, and ZSM-35 prepared in accordance with Example 3 above were used in 1-butene skeletal isomerization reactions at 400° C. and varying n-butene conversions over a wide range of process conditions. FIG. 3 is a selectivity/conversion plot comparing the performance of the two catalysts. At 30 to 40% conversion, selectivity of ZSM-23 ranges between 30 and 80%. In contrast, selectivity of ZSM-35 ranges from 90 to 99%. Indeed, selectivity of ZSM-35 remains relatively flat at greater than 85% all the way from about 2 to 40% conversion.

Example 8
Isomerization of 1-Butene with HZSM-35/$SiO_2$ Mix

The ZSM-35-containing catalyst of Example 2 was used to process a 1-butene feed under four sets of skeletal isomerization conditions comprising two temperatures and two relatively low 1-butene partial pressures. The conditions and compositions of the product streams from Runs 1 to 4 are set out in Table 1 below. Selectivity for isobutene ranged from 93.2 to 99%.

TABLE 1

Butene Skeletal Isomerization Using ZSM-35/SiO$_2$ Mix
Catalyst: ZSM-35/Silica Mixed (65/35), Silica/Alumina = 20,
Catalyst Alpha = 96
Feed: 1-Butene/Nitrogen

| Run Number: | 1 | 2 | 3 | 4 |
|---|---|---|---|---|
| Feed 1-Butene WHSV: | 76 | 75 | 21 | 21 |
| Feed Nitrogen/1-Butene (vol/vol) | 3 | 3 | 10 | 10 |
| Temperature (°C.) | 400 | 550 | 400 | 550 |
| Pressure (kPa) | 163 | 170 | 156 | 163 |
| Hours On Stream | 2 | 6 | 9 | 14.5 |
| Composition of the Product Stream (%) | | | | |
| Normal Butenes | 61.9 | 62.9 | 66.8 | 62.2 |
| Isobutene | 35.5 | 35.2 | 32.9 | 36.2 |
| Propene | 1.1 | 0.6 | 0.2 | 0.4 |
| Pentenes | 0.8 | 0.3 | 0 | 0 |
| Other C$_{5-}$ | 0.7 | 0.9 | 0.1 | 1.2 |
| C$_{6+}$ | 0 | 0.1 | 0 | 0 |
| n-Butene Conversion (%) | 38.1 | 37.1 | 33.2 | 37.8 |
| Isobutene Selectivity (%) | 93.2 | 95 | 99 | 95.6 |

Example 9

Isomerization of 1-Butene with Silica-Bound ZSM-35

The ZSM-35-containing catalyst of Example 3 was used to process a 1-butene feed under four sets of skeletal isomerization conditions comprising two temperatures and two relatively low 1-butene partial pressures. The conditions and compositions of the product streams from Runs 1 to 4 are set out in Table 2 below. A comparison of Tables 1 and 2 shows that silica binding has no significant deleterious effect on performance between silica-bound ZSM-35 and ZSM-35/SiO$_2$ mix catalysts.

TABLE 2

Butene Skeletal Isomerization Using Silica-Bound ZSM-35
Feed: 1-Butene/Nitrogen

| Run Number: | 1 | 2 | 3 | 4 |
|---|---|---|---|---|
| Feed 1-Butene WHSV: | 65.9 | 65.5 | 18.4 | 18.5 |
| Feed Nitrogen/1-Butene (vol/vol) | 3 | 3 | 10 | 10 |
| Temperature (°C.) | 400 | 550 | 400 | 550 |
| Pressure (kPa) | 161 | 171 | 158 | 165 |
| Hours On Stream | 2.5 | 6.5 | 9.5 | 14.5 |
| Composition of the Product Stream (%) | | | | |
| Normal Butenes | 65 | 63.3 | 64.5 | 63 |
| Isobutene | 32.8 | 34.8 | 35.1 | 36.0 |
| Propene | 0.84 | 0.6 | 0.2 | 0.48 |
| Pentenes | 0.65 | 0.25 | 0 | 0 |
| Other C$_{5-}$ | 0.62 | 0.94 | 0.2 | 0.55 |
| C$_{6+}$ | 0.1 | 0.13 | 0 | 0 |
| n-Butene Conversion (%) | 35 | 36.7 | 35.5 | 37 |
| Isobutene Selectivity (%) | 93.7 | 95 | 98.9 | 97.2 |

Example 10

1-Butene Conversion at Low Temperature, High Pressure Conditions

1-Butene was converted over the HZSM-35 catalyst of Example 4 under the following conditions:

| | |
|---|---|
| Temperature | 400° C. |
| Pressure | 200 kPa |

-continued

| | |
|---|---|
| 1-Butene WHSV | 20 to 65 hr$^{-1}$ |
| Total WHSV | 40 to 130 hr$^{-1}$ |
| N$_2$/Butene | 1 (vol/vol) |

The results of this conversion are depicted in FIG. 4 and show that ZSM-35, unlike ZSM-22 and ZSM-23, performs well, particularly respecting selectivity, even at high WHSV, low temperatures and high butene partial pressures.

Example 11

1-Pentene Conversion over ZSM-35

1-Pentene was converted over the ZSM-35/SiO$_2$ catalyst of Example 3 under the following conditions:

| | |
|---|---|
| Temperature | 400° C. |
| Pressure | 200 kPa |
| 1-Pentene WHSV | 123 hr$^{-1}$ |
| Hours On Stream | 10. |

This conversion yielded the following product distribution (wt %):

| | |
|---|---|
| Total C4— | 1.7 |
| 2-methyl-1-butene | 19.4 |
| 2-methyl-2-butene | 51.5 |
| 3-methyl-1-butene | 0.1 |
| 1-pentene | 2.2 |
| trans-2-pentene | 14.9 |
| cis-2-pentene | 9.6 |
| Total C6+ | 0.7 |
| IC5=/NC5= in product | 2.66. |

The above results indicate that linear pentene is converted to branched pentenes (to near equilibrium) over ZSM-35 with excellent selectivity.

While the instant invention has been described by specific examples and embodiments, there is no intent to limit the inventive concept except as set forth in the following claims.

It is claimed:

1. A method for highly selective conversion of linear olefins to corresponding iso-olefins of the same carbon number which comprises contacting a linear olefin-containing organic feedstock comprising C$_4$ to C$_{10}$ linear olefins with a catalyst comprising ZSM-35 under skeletal isomerization conditions.

2. The method of claim 1 wherein said conversion is carried out at temperatures between about 250° and 750° C., weight hourly space velocities based on linear olefins in said feedstock between 5 and 500 WHSV, and linear olefin partial pressures between 12 and 500 kPa.

3. The method of claim 2 wherein said conversion is at least 10 wt % and has a linear olefin to iso-olefin selectivity of at least 70 wt %.

4. The method of claim 2 wherein said conversion is at least 10 wt % and has a linear olefin to iso-olefin selectivity of at least 80 wt %.

5. The method of claim 1 wherein said conversion is carried out at temperatures between about 325° and 600° C., weight hourly space velocities based on linear olefin in said feedstock between 10 and 400 WHSV; and linear olefin partial pressures between 30 and 300 kPa.

6. The method of claim 5 wherein said conversion is at least 25 wt % and has a linear olefin to iso-olefin selectivity of at least 75 wt %.

7. The method of claim 5 wherein said conversion is at least 25 wt % and has a linear olefin to iso-olefin selectivity of at least 85 wt %.

8. The method of claim 1 wherein said conversion is carried out at temperatures between about 390° and 550° C., weight hourly space velocities based on linear olefin in said feedstock between 30 and 250 WHSV; and linear olefin partial pressures between 30 and 150 kPa.

9. The method of claim 8 wherein said conversion is at least 35 wt % and has a linear olefin to iso-olefin selectivity of at least 80 wt %.

10. The method of claim 8 wherein said conversion is at least 35 wt % and has a linear olefin to iso-olefin selectivity of at least 90 wt %.

11. The method of claim 1 wherein linear olefin to iso-olefin selectivity is at least 92% at a conversion temperature less than or equal to 400° C. and linear olefin partial pressure above 2 psia (14 kPa).

12. The method of claim 1 wherein linear olefin to iso-olefin selectivity is at least 90% at a conversion temperature less than or equal to 400° C. and linear olefin partial pressure above 5 psia (34 kPa).

13. The method of claim 1 wherein linear olefin to iso-olefin selectivity is at least 95% at a conversion temperature less than or equal to 550° C. and linear olefin partial pressure above 5 psia (34 kPa) at an overall conversion of linear olefins of at least 30 wt %.

14. The method of claim 1 wherein said conversion results in less than 30% conversion to products of lower or higher average carbon number.

15. The method of claim 1 wherein said conversion results in less than 5% conversion to products of lower or higher average carbon number.

16. The method of claim 1 wherein said feedstock comprises $C_4$ to $C_6$ linear olefins.

17. The method of claim 1 wherein said catalyst is reactivated by exposure to hydrogen at temperatures of at least 400° C. for a time sufficient to effect reactivation.

18. The method of claim 1 wherein said catalyst is reactivated by exposure to oxygen at temperatures of at least 350° C. for a time sufficient to effect reactivation.

19. The method of claim 1 wherein said catalyst comprises 10 to 99 wt % of a refractory inorganic oxide binder.

20. The method of claim 1 wherein said catalyst comprises 20 to 70 wt % of a silica binder.

21. The method of claim 1 wherein said catalyst comprises 20 to 70 wt % of an alumina binder.

22. The method of claim 1 wherein said organic feedstock comprises at least 5 wt % n-butenes.

23. The method of claim 1 wherein said organic feedstock comprises cracking process light gas.

24. The method of claim 1 wherein said organic feedstock consists essentially of a $C_4$ hydrocarbon stream.

25. The method of claim 1 wherein said organic feedstock consists essentially of a $C_{4+}$ hydrocarbon stream.

26. The method of claim 1 wherein said catalyst has an alpha value of at least 5.

* * * * *